United States Patent [19]

Haber

[11] Patent Number: 4,686,962

[45] Date of Patent: Aug. 18, 1987

[54] DISPOSABLE CARTRIDGE ASSEMBLY FOR HYPODERMICALLY IMPLANTING A GENITOURINARY PROSTHESIS

[75] Inventor: Terry M. Haber, Lake Forest, Calif.

[73] Assignee: Habley Medical Technology Corporation, Laguna Hills, Calif.

[21] Appl. No.: 882,086

[22] Filed: Jul. 3, 1986

[51] Int. Cl.$^4$ ............................................. A61B 19/00
[52] U.S. Cl. ................................. 128/1 R; 128/325; 128/DIG. 25; 604/97; 604/274
[58] Field of Search ........................ 604/51, 57, 58, 60, 604/97–99, 274; 128/1 R, 1.3, 129, DIG. 25, 325, 344

[56] References Cited

U.S. PATENT DOCUMENTS

| | | | |
|---|---|---|---|
| 2,921,580 | 1/1960 | Indelicato | 128/129 |
| 3,675,639 | 7/1972 | Cimber | 128/1 R |
| 3,722,500 | 3/1973 | Robinson | 128/1 R |
| 3,795,246 | 3/1974 | Sturgeon | 128/325 |
| 4,005,699 | 2/1977 | Bucalo | 128/1.3 |
| 4,019,499 | 4/1977 | Fitzgerald | 128/1 R |

OTHER PUBLICATIONS

"Polytef (Teflon) Migration after Periurethal Injection: Tracer and X-ray Microanalysis Techniques in Experimental Study" by A. A. Malizia, Jr. et al, vol. XXX, *Trans. Am. Soc. Artif. Intern. Organs,* 1983, pp. 330–334.
"Migration and Granulomatous Reaction after Periurethral Injection of Polytef (Teflon)" by Anthony A. Malizia, Jr. et al, vol. 251, *Journal of the A.M.A.,* Jun. 22/29, 1984, pp. 3277–3281.
"Periurethral Polyetrafluoroethylene Injections in Incontinent Female Subjects with Neurogenic Bladder Disease" by Robert I. Lewis et al, vol. 131, *Journal of Urology,* Mar. 1984, pp. 459–462.
"Periurethral Polytetrafluoroethylene Injection for Urinary Incontinence" by Victor A. Politano, vol. 127, *Journal of Urology,* Mar. 1982, pp. 439–442.
"Endoscopic Injections of Teflon to Treat Urinary Incontinence in Women", *British Medical Journal,* vol. 288, Jan. 21, 1984, p. 192.

*Primary Examiner*—Dalton L. Truluck
*Attorney, Agent, or Firm*—Morland C. Fischer

[57] ABSTRACT

A non-surgical method for implanting a genitourinary prosthesis comprising an extensible, inflatable tissue expanding containment membrane to be located between the urethra and the subcutaneous corpus spongiousum of a patient to overcome urinary incontinence by means of localized, controlled tissue volume increase. A disposable cartridge assembly is also disclosed for hypodermically positioning, injecting and inflating the containment membrane and for percutaneously infusing the membrane with biocompatible fluid or suspended particulate matter. The containment membrane functions as an envelope for retaining the fluid or suspended particulate matter therewithin while simultaneously increasing localized tissue volume and advantageously preventing the migration of such fluid or particles through the patient's body. Accordingly, an increased passive occlusive pressure may be applied to the patient's urethra to return the patient to continence.

19 Claims, 3 Drawing Figures

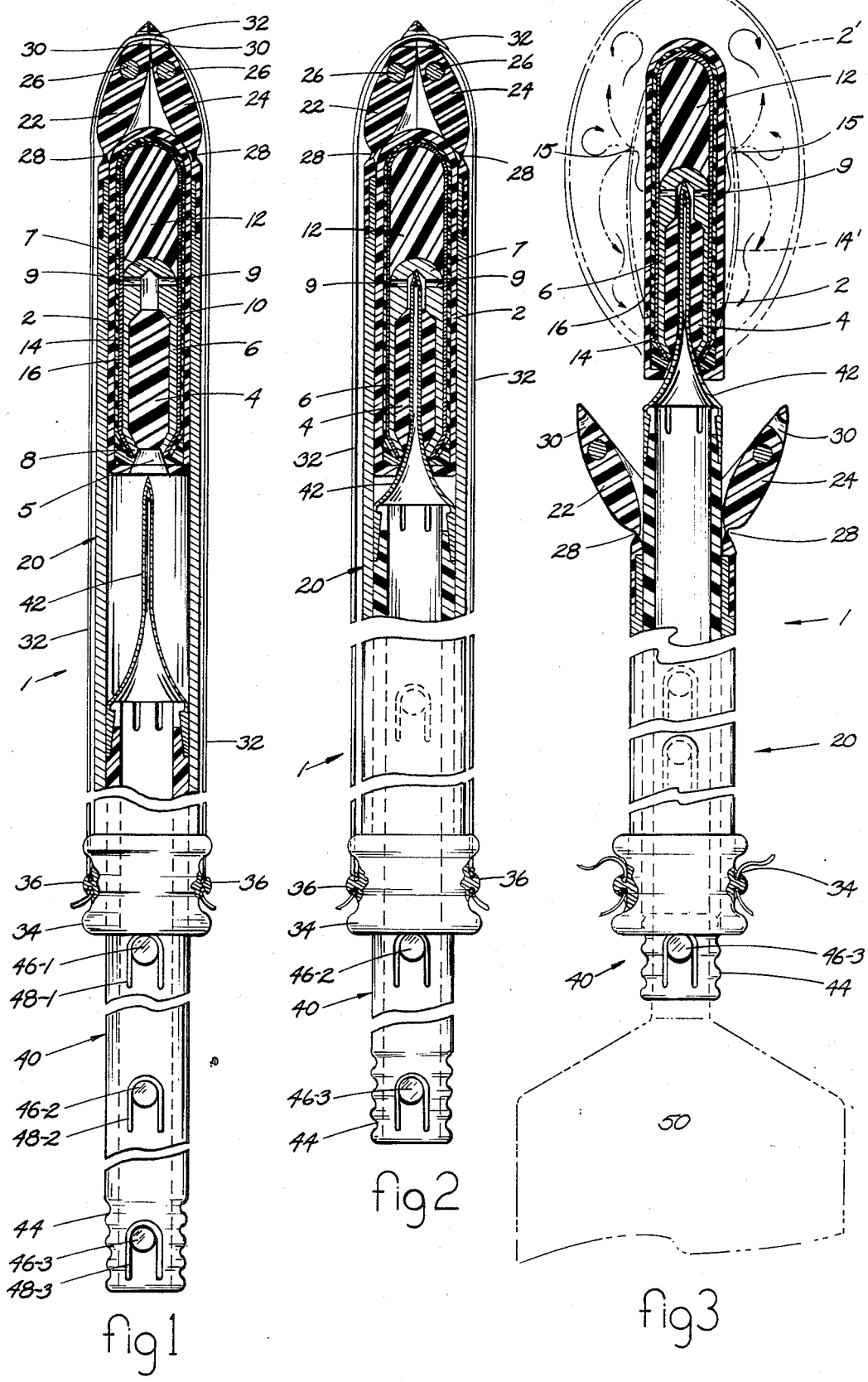

DISPOSABLE CARTRIDGE ASSEMBLY FOR HYPODERMICALLY IMPLANTING A GENITOURINARY PROSTHESIS

BACKGROUND OF THE INVENTION

1. Field of the Invention

This invention relates to an inflatable genitourinary prosthesis and to a disposable cartridge assembly for hypodermically positioning, injecting and inflating the prosthesis so that increased occlusive pressure may be controllably applied to a patient's urethra for holding the patient continent. The prosthesis includes an expandable antimigration membrane which may be percutaneously infused with fluid or suspended particulate matter so as to simultaneously increase localized tissue volume while preventing the possible migration of such fluid or suspended particulate matter.

2. PRIOR ART

As will be known to those skilled in the art, in cases where the natural sphincter muscles of a patient have been surgically excised, damaged by disease or compromised by physical trauma, an artificial prosthetic sphincter has often been implanted so that occlusive pressure may be applied to the urethra to restore continence. Artificial sphincters are well-known and specific examples thereof will not be listed. However, the implantation of an artificial sphincter commonly requires a surgical procedure which necessitates the hospitalization of the patient. Such a procedure is relatively complex and expensive, and usually requires six to eight weeks or more of recovery time. Accordingly, both the patient and his physician face approximately two months of delay before being able to actuate the prosthesis to ascertain whether the surgery has been successful and the patient is continent. More particularly, because of the swollen and aggravated condition of edema of the urethral tissues during and for a period subsequent to surgery, the physician cannot precisely match the occlusisve pressure available from the prosthetic sphincter to the patient's urethra. Therefore, the physician must estimate the required minimal occlusive pressure needed to achieve urethral coaptation in that particular patient. As a consequence of such estimate, sphincteric mechanisms are often improperly selected or fitted, so that the occlusive pressures generated by such mechanisms are either insufficient to successfully achieve continence or excessive to the point of causing ischemia and subsequent erosion of urethral tissue. Excessive occlusive forces may undesirably minimize arteriovascular blood flow to the urethra and thereby cause ischemia and subsequent erosion of the delicate tissues. What is more, if the implant surgery should prove to be unsuccessful (i.e. the maximum occlusive pressure to be generated by the sphincter is insufficient to hold the patient continent or the sphincter malfunctions mechanically), then additional surgery becomes necessary to provide sphincter adjustment, repair or explant.

In the recent past, it has been suggested that urinary incontinence may be successfully treated by non-surgical means with the periurethral injection of TEFLON paste (e.g. "POLYTEF") to increase localized tissue volume and thereby increase the available occlusive pressure to be applied to the urethral mucosa of an incontinent patient. However, this suggested treatment may lead to potential problems as a consequence of the migration of the paste from the injection site. That is, such paste has been known to induce tissue reaction and form TEFLON-induced granulomas in certain individuals. Because of the possible tissue reaction to TEFLON-based paste, concern for patient safety has also been expressed. Hence an otherwise advantageous, non-surgical procedure has now fallen into some disfavor.

SUMMARY OF THE INVENTION

Briefly, and in general terms, this invention relates to a non-surgical procedure for successfully treating urinary incontinence. More particularly, a unique genitourinary prosthesis comprising an extensible and inflatable, elliptoidally shaped containment membrane is perineally or periurethrally injected to form an enclosure for receiving and retaining a supply of fluid or suspended particulate matter. In this manner, the membrane is precisely and controllably inflated while in situ so as to cause increased localized tissue volume and correspondingly greater occlusive pressure to the underlying urethral mucosa to restore the patient to continence. However, the existing problem of particle migration is solved by virtue of the anti-migration membrane in which the fluid or suspended particulate matter is retained.

The genitourinary prosthesis of this invention is hypodermically implanted by means of a disposable cartridge assembly for subcutaneously inflating the containment membrane. The cartridge assembly includes an outer trocar tube to dilate a suitably sized insertion channel through the targeted patient tissues. Located within the outer trocar is the containment membrane in an uninflated state. Also located within the outer trocar and spaced behind the containment membrane is an inner stylus tube having a hypodermic needle affixed to one end thereof. The inner stylus is controllably advanced through the outer trocar from one predetermined position to another for placing the hypodermic needle in communication with the interior of the uninflated containment membrane and for sliding the containment membrane outwardly from the trocar to a suitable position at the bulbar urethra, at which position the membrane is percutaneously infused by and inflated with a measured volume of fluid or suspended particulate matter via the hypodermic needle. An inflation of the membrane proportionately increases local tissue volume in the area of the proximal corpus spongiousum to correspondingly increase the occlusive pressure applied to the urethral tissues for restoring a patient to continence. The positioning, injecting and inflating cartridge assembly is then withdrawn from the urethral tissue leaving the inflated containment membrane to form an envelope for preventing the undesirable migration of the fluid or suspended particulate matter. One or more of the genitourinary prostheses of the present invention may be implanted, as just described, depending upon etiology, degree of residual sphincteric function, vascularity and physical properties of that individual patient's urethral tissues.

BRIEF DESCRIPTION OF THE DRAWINGS

FIG. 1 shows the disposable cartridge assembly of the present invention having a closed cutting nose and an uninflated tissue expanding containment membrane located behind the cutting nose;

FIG. 2 shows the cartridge assembly of FIG. 1 with a hypodermic needle thereof positioned at the interior of the containment membrane just prior to percutaneously infusing the membrane with fluid or suspended particulate matter;

FIG. 3 shows the cartridge assembly of FIG. 2 with the cutting nose thereof opened and the containment membrane advanced outwardly therepast and inflated with a measured supply of fluid or suspended particulate matter by way of said hypodermic needle.

DESCRIPTION OF THE PREFERRED EMBODIMENT

Referring concurrently to FIGS. 1, 2 and 3 of the drawings, there is shown a disposable cartridge assembly 1 for hypodermically implanting a self-contained, inflatable genitourinary prosthesis at a suitable location (e.g. between the urethra and the subcutaneous corpus spongiousum of a patient) to overcome urinary incontinence by means of localized, controlled tissue volume increase. The genitourinary prosthesis of the present invention comprises an elastomeric, elliptoidally-shaped containment membrane 2. Containment membrane 2 is preferably formed from an extensible, tear-resistant, biocompatible material, such as, for example, polyurethane, silicone, latex, or the like. In FIGS. 1 and 2, containment membrane 2 is shown in the preinjected, uninflated state (i.e. devoid of fluid and/or suspended particulate matter). In FIG. 3, containment membrane 2' is shown in the injected, inflated state (i.e. filled with biocompatible fluid and/or suspended particulate matter).

Located at the interior of containment membrane 2 is a valve plug 4 of solid cross-section. Valve plug 4 is preferably formed from an elastomeric polymer material that is characterized by a high spring constant and coefficient of elasticity and low durometer, such as silicone, or the like. Surrounding the valve plug 4 is a tubular needle stop 6. In the assembled relationship, the needle stop 6 exerts high compressive pressure upon the valve plug 4 to increase the functional density thereof and thereby promote an efficient self-healing of any post-implant puncture channel that may be formed therein. The needle stop 6 is preferably formed from a tensile force-resistant, bicompatible, radio-opaque and noncorrosive material, such as, for example, tantalum.

Needle stop 6 has a closed hemispheric first end 7 and an open opposite end 8. The open end 8 of needle stop 6 forms a conical entry port 5 to permit the tip of a hypodermic needle 42 to be inserted into and through the valve plug 4, as will be described in greater detail when referring specifically to FIG. 2. The hemispheric end 7 of needle stop 6 forms a stop to limit the forward movement of the hypodermic needle 42 towards the containment membrane 2. Hence, needle stop 6 prevents the hypodermic needle from accidentally penetrating the containment membrane and thereby avoids the possibility of leaking migratory fluid or suspended particulate matter into the patient's body, a problem which is common to other non-surgical medical attempts to overcome urinary incontinence. The hemispheric end 7 is provided with a suitable number of delivery ports 9 extending therethrough. As will be described in greater detail when referring specifically to FIG. 3, such delivery ports permit communication between the hypodermic needle 42 and the interior of containment membrane 2 during the inflation of the membrane by fluid or suspended particulate matter. The hemispheric end 7 is also provided with a shoulder 10 of reduced diameter so as to receive the valve plug 4 thereagainst and limit any forward movement of the plug to avoid a blockage of the delivery ports 9 when the tip of hypodermic needle 4 is inserted through valve plug 4.

Also located at the interior of containment membrane 2 above the closed hemispheric end 7 of needle stop 6 is a volume increasing rod 12. Rod 12 functions to reduce the stress upon and increase the ultimate volumetric capacity within containment membrane 2 when such membrane is filled with fluid or suspended particulate matter in the inflated state of FIG. 3. Rod 12 also functions as a preform for containment membrane 2 to prevent the collapse thereof when in the uninflated state of FIGS. 1 and 2 and avoid the possibility of blocking material flow to the membrane interior. Surrounding the needle stop 6 and the volume increasing rod 12 is an extensible, unidirectional flow control and sealing membrane 14. Membrane 14 is provided with several punctures (designated 15 in FIG. 3) which form a flow path with the delivery ports 9 of needle stop 6 through which fluid or suspended particulate matter may pass, under presure, to inflate containment membrane 2.

The puncture 15 serve as unidirectional flow valves which are opened by expansive tensile forces to permit fluid or suspended particulate matter to be injected from the hypodermic syringe 42 into containment membrane 2 but are otherwise closed by hydraulic back pressure against the needle stop 6 to prevent the backflow or leakage of fluid or particles from an inflated containment membrane 2' (of FIG. 3). Thus, it may be appreciated that the aforementioned flow control membrane 14 and the previously mentioned valve plug 4 form redundant, antileakage seals to reduce the probability of deflation of containment membrane 2 and the undesirable migration of fluid or suspended particulate matter through the body of the patient. A layer of release film 16 (e.g. polyethylene) is applied between the containment and flow control membranes 2 and 14 to prevent such membranes from sticking together during the manufacture of the cartridge assembly.

Hypodermic positioning, injecting and inflating instruments of the cartridge assembly 1 are now disclosed for implanting the tissue expanding containment membrane 2 and percutaneously infusing the membrane with fluid or suspended particulate matter. The instruments include a hollow, cylindrical outer trocar 20 and a hollow, cylindrical inner stylus 40 located within and slidable through trocar 20. The distal end of outer trocar 20 houses the tissue expanding membrane 2 therewithin and functions, in part, as a removable outer casing to protect the integrity of and guide the containment membrane 2 during implantation. Such distal end terminates at a non-coring cutting nose comprising a pair of cutting members 22 and 24. The outer trocar 20 and the cutting members 22 and 24 are preferably formed from a rigid, corrosion-resistant polymeric biomaterial, such as acetal homopolymer, or the like. A radioopaque placement indicator 26 is disposed within each cutting member 22 and 24 so that the subcutaneous location of the cutting nose of trocar 20 can be fluoroscopically monitored. A first end of each of the cutting members 22 and 24 is respectively connected to trocar 20 at an integral continuous hinge 28. Thus, and as will be described in greater detail when referring specifically to FIG. 3, the cutting members 22 and 24 are adapted to pivot around their respective hinges 28 and out of the way of containment membrane 2 so as to permit the membrane to be moved outwardly through the distal end of trocar 20.

In the assembled cartridge relationship shown in FIGS. 1 and 2, the second ends of the cutting members 22 and 24 are tied together to form a sharp and non-coring cutting surface for penetrating the urethral tissues of the targeted patient and thereby establishing a tunnel through which the containment membrane 2 may be suitably positioned and implanted (e.g. within the bulbar urethra of the corpus spongiousum). The cutting members 22 and 24 have a short aperture 30 formed therein. An elongated piece of biomeric material (e.g. a surgical suture) 32 extends through the apertures 30 to releasably secure the cutting members together (i.e. in a clamshell configuration) to thereby form the cutting nose of outer trocar 20.

More particularly, the proximal end of trocar 20 terminates at an enlarged gripping portion 34 which is of suitable size and shape to facilitate the handling of trocar 20 by a physician. A pair of suture anchors 36 are disposed on opposite sides of gripping portion 34. A first end of the aforementioned surgical suture 32 is securely tied to one suture anchor 36. The second end of suture 32 is passed through the apertures 30 formed in the cutting members 22 and 24 and securely tied to the other anchor 36. Sufficient tension is applied to suture 32 so as to preserve the noncoring configuration of the trocar cutting nose during insertion of the cartridge assembly 1.

The inner stylus 40 is formed from a suitable biomeric material, such as polycarbonate, or the like and is located within and slidable through outer trocar 20, as previously disclosed. Affixed to the distal end of stylus 40 is a hollow, stainless steel hypodermic needle 42 by which to percutaneously infuse containment membrane 2 with a premeasured supply of fluid or suspended particulate matter, whereby to inflate membrane 2 and increase the occlusive pressure being applied to the urethra for returning the patient to continence. The proximal aspect of hypodermic needle 42 is preferably provided with a hyperbolic configuration to enhance the deflective resistance of needle 42 with respect to valve plug 4 (best shown in FIGS. 2 and 3). The proximal end of stylus 40 is provided with a grip 44 which is of suitable size and shape to facilitate the handling of stylus 40 by a physician.

A series of (three) position control stops 46-1, 46-2 and 46-3 extend outwardly from stylus 40 in alignment with one another along the longitudinal axis of stylus 40. The control stops 46 are peg-shaped projections which are located at particular predetermined positions along stylus 40 for the purpose of permitting the physician to accurately and automatically control the advancement of inner stylus 40 relative to outer trocar 20 for successively positioning, injecting and inflating the containment membrane according to a non-surgical method to be described in greater detail hereinafter.

In the assembled cartridge relationship and in their relaxed condition, the control stops 46 extend above the surface of inner stylus 40 so as to be received against the proximal grip end 34 of outer trocar 20 and thereby limit the movement of stylus 40 through trocar 20. Control stops 46 are preferably molded during the formation of stylus 40. During such formation, respective troughs 48-1, 48-2 and 48-3 are established around stops 46-1, 46-2 and 46-3 to provide the stops with flexibility and the ability to be pressed downwardly and into the stylus 40.

The operation of the cartridge assembly 1 and the nonsurgical method for positioning, injecting and inflating the containment membrane 2 which forms the prosthesis of this invention are now described while continuing to refer to FIGS. 1-3 of the drawings. FIG. 1 shows the cartridge assembly 1 with the inner stylus 40 located inside and coaxially aligned with the outer trocar 20. A first of the position control stops 48-1 is received against the proximal end 34 of trocar 20 so as to simultaneously retain stylus 40 at a first predetermined position with respect to trocar 20 and locate hypodermic needle 42 in spaced, coaxial alignment with valve plug 4. In such a predetermined position, the physician exerts a downward force on the cartridge assembly 1 to transurethrally or perineally insert the cutting nose of trocar 20 through the patient's tissue.

Referring now to FIG. 2, the physician depresses the first position control stop 46-1 so as to force the stop downwardly into stylus 40 to permit the movement of inner stylus 40 with respect to outer trocar 20. The physician then advances the stylus 40 through trocar 20 until a second of the position control stops 48-2 is received against the proximal end 34 of trocar 20 so as to simultaneously retain stylus 40 at a second predetermined position with respect to trocar 20 and force hypodermic needle 42 into and through the valve plug 4 at the interior of containment membrane 2. In such a second predetermined position, the tip of hypodermic needle 42 is disposed adjacent the closed hemispheric end 7 of needle stop 6 and in communication with the interior of membrane 2 by way of delivery ports 9.

Referring now to FIG. 3, the physician verifies the location of cutting members 22 and 24 which form the cutting nose of the trocar 20 so that containment membrane 2 may be properly positioned within the tissues of the corpus spongiousum. The physician then cuts the suture 32 (in the area of trocar grip 34) and removes the suture tie from the apertures 30 of cutting members 22 and 24. Next the physician depresses the second position control stop 46-2 so as to force the stop downwardly into stylus 40 to again permit the movement of inner stylus 40 with respect to outer trocar 20. The physician advances stylus 40 through trocar 20 until the third position control stop 46-3 is received against the proximal end 34 of trocar 20 so as to simultaneously separate the cutting members 22 and 24 and move the containment membrane 2 forward and out of the trocar. That is, with suture 32 removed from the cartridge assembly 1, the cutting members 22 and 24 are free to rotate around their respective hinges 28 and out of the way of the advancing containment membrane 2.

As also shown in FIG. 3, the physician attaches a high pressure hypodermic syringe 50 at the proximal end 44 of stylus 40. Hypodermic syringe 50 contains a measured supply of fluid or suspended particulate matter, such as radio opaque isotonic fluid, isotonic saline solution, suspended (e.g. TEFLON) particles or spheres, and the like, a regulated amount of which is to be percutaneously infused to the interior of containment membrane 2. Accordingly, a flow path is established between hypodermic syringe 50 and the interior of containment membrane 2 by way of stylus 40, hypodermic needle 42, fluid ports 9, and the small punctures 15 formed in flow control membrane 14. Thus, the physician may infuse the containment membrane 2 with a controlled and measured volume of fluid or suspended particulate matter to inflate the membrane (designated 2' in the inflated condition) and thereby produce increases in localized tissue volume and passive occlusive pressures sufficient to occlude the urethra and return the patient to urinary continence. In this manner, the containment membrane may be precisely and controllably infused with the minimum volume of fluid or suspended particulate matter necessary to achieve coaptive continence (contact) of the urethral mucosa while minimizing the risk of impeding arteriovascular blood flow through the patient's urethra as a consequence of ischemia. Moreover, the inflated containment membrane 2' serves as a non-permeable envelope for preventing the migration of the contained fluid or suspended particulate matter through the body of the patient.

As is best shown in FIG. 3, during the inflation of containment membrane 2, the flow control membrane (designated 14') is forced outwardly and stretched away from needle stop 6 so as to open punctures 15 to the passage therethrough of the fluid or suspended particulate matter from hypodermic syringe 50. However, at the conclusion of inflating membrane 2, the fluid control membrane 14 returns to its relaxed and unstretched condition adjacent needle stop 6 because of internal fluid pressure as well as its own elastomeric memory which effectively closes the punctures 15 to material flow and prevents the escape of material from and the possible deflation of membrane 2, an advantage which was previously pointed out when describing the redundant anti-leakage seals provided by membrane 14 and valve plug 4.

The physician then exerts an upward pulling force at stylus grip 44 to release and remove the inner stylus 40 and the hypodermic needle 42 which is attached thereto. Removal of inner stylus 40 from outer trocar 20 permits the cutting members 22 and 24 to rotate back and forth around their respective hinges 28 to facilitate the removal of trocar 20. By exerting an upward pulling force at trocar grip 34, the physician may remove trocar 20, and thereafter, close the trocar puncture wound, whereby to complete the non-surgical method for implanting the presently disclosed prosthesis. At this point, the physician may dispose of both the trocar 20 and stylus 40.

It may be noted that removal of cartridge assembly 1 from the patient's urethral tissue will leave behind a relatively minor puncture wound. Thus, as another important advantage of this invention, the patient will require a substantially shorter recovery time or no recovery time at all as compared to approximately two months or more if a prosthetic sphincter had been surgically implanted in a hospital. Moreover, the high cost, confinement, and inconvenience commonly associated with such a hospital stay can be eliminated since the present prosthesis can be injected under a local anesthetic and the patient treated on a relatively cost-effective out-patient basis.

Although the presently disclosed invention has been explained with reference to a single, implantable tissue expanding containment membrane 1, it is to be expressly understood that any number of such containment membranes may be implanted, depending upon the increased tissue volume and resulting occlusive pressure which are required to permit the patient to be restored to continence. During and after one or more prostheses have been implanted, the physician may cystoscopically monitor the patient's degree of contact of the urethral mucosa. In the event that greater occlusive pressure is needed, the physician may implant a corresponding additional number of prostheses until patient continence is restored. That is, the physician merely opens a sterile container (not shown) in which each disposable cartridge assembly 1 is conveniently packaged and again performs the previously described non-surgical implant procedure.

It will be apparent that while a preferred embodiment of the invention has been shown and described, various modifications and changes may be made without departing from the true spirit and scope of the invention. For example, the containment membrane has applications other than as an injectable prothesis for restoring a patient to urinary continence. More particularly, the containment membrane may be formed from a selectively permeable (by a gas or liquid) material which can be implanted as a drug delivery system. Other applications include that of a variable volume mass to replace surgically removed tissue and/or organ excisions or as an injectable antiureteral reflux mass. Still further applications of the present invention include an injectable testicular prothesis, injectable prosthetic eye, prosthetic sphincter and injectable intraocular lens. Of course, the prosthesis of this invention is also applicable for controllably occluding luminal passages other than the patient's urethra when it is necessary to selectively control the flow of material therethrough.

Having thus set forth the preferred embodiment of this invention, what is claimed is:

1. An assembly for hypodermically implanting a genitourinary prosthesis for the treatment of urinary incontinence, said assembly comprising:

outer tube means having a cutting end for penetrating the urethral tissues of a patient undergoing treatment, said cutting end including a non-coring cutting nose disposed in a normally closed position across said outer tube means;

said genitourinary prosthesis comprising an inflatable containment membrane located within said outer tube means behind the cutting end thereof; and inner tube means located within and slidable through said outer tube means for opening said cutting nose, said inner tube means having a hypodermic needle at one end thereof and means for advancing said inner tube means through said outer tube for placing said hypodermic needle in communication with the interior of said containment membrane and for moving said containment membrane outwardly from the cutting end of said outer tube means, said containment membrane being percutaneously infused with and inflated by a supply of material by way of said hypodermic needle to increase local tissue volume and occlusive pressure applied to the urethra for returning the patient to continence.

2. The assembly recited in claim 1, wherein said cutting nose comprises at least first and second cutting members pivotably attached to said outer tube means and rotatable from a closed position across said outer tube means for penetrating the urethral tissues to an opened position for permitting said containment membrane to be moved outwardly from the cutting end of said outer tube means.

3. The assembly recited in claim 2, further including means for releasably connecting said first and second cutting members together in the closed position across said outer tube means.

4. The assembly recited in claim 3, wherein said means for releasably connecting said first and second cutting members together is a suture passing through an aperture formed in each of said cutting members and extending along opposite sides of said outer tube means, said suture being removable from the apertures of said cutting members for permitting said cutting members to move apart from one another and rotate from the closed to the opened position.

5. The assembly recited in claim 1, wherein a portion of said inner tube means extends outwardly from an end of said outer tube means opposite the cutting end thereof, said inner tube means portion having a plurality of position control stops aligned with one another along the longitudinal axis of said inner tube means and projecting above the surface of said inner tube means to be received against the end of said outer tube means opposite said cutting end for limiting the movement of said inner tube means through said outer tube means.

6. The assembly recited in claim 5, further including means by which selected ones of said position control stops are moved out of the way of said outer tube means to permit said inner tube means to be moved through said outer tube means from one predetermined position to another, at which positions said hypodermic needle is placed in communication with said containment membrane and said containment membrane is moved outwardly from the cutting end of said outer tube means.

7. The assembly recited in claim 1, further comprising a needle stop located between a material delivery end of said hypodermic needle and said containment membrane to prevent the accidental puncture of said membrane by said needle, said needle stop having at least one opening formed therethrough to permit the delivery of material by way of said hypodermic needle to the interior of said membrane.

8. The assembly recited in claim 7, further including an extensible flow control membrane having a normally closed puncture formed therein and being positioned between the opening in said needle stop and the interior of said containment membrane, said flow control membrane being expanded during the inflation of said containment membrane with material, whereby to open said puncture and permit the passage of material from said hypodermic needle to the interior of said containment membrane by way of the opening in said needle stop and said puncture.

9. The assembly recited in claim 1, further including a plug means located in an inlet end of said containment membrane, said hypodermic needle being removably inserted into and releasably positioned by said plug means so that material can be delivered to the interior of said containment membrane, said plug means forming a fluid-tight closure at the inlet end of said membrane to prevent the escape of material after said membrane has been inflated and said needle has been removed.

10. A non-surgical method for implanting a prosthesis comprising an inflatable containment membrane for increasing the occlusive pressure applied to a patient's urethra for treating urinary incontinence, said method comprising the steps of:
 piercing a small tunnel through the patient's urethral tissues with a hollow piercing instrument;
 sliding an uninflated containment membrane through the interior of said cutting instrument and locating said membrane proximally adjacent to the patient's urethral mucosa;
 percutaneously infusing said containment membrane with a supply of material from a source thereof by way of said piercing instrument to inflate said membrane and thereby increase the occlusive pressure applied to said urethral mucosa; and
 removing said piercing instrument from the urethral tissues.

11. The method recited in claim 10, comprising the additional steps of positioning a hypodermic needle within said hollow piercing instrument and sliding said needle through said piercing instrument and into communication with the interior of said containment membrane prior to the step of sliding and locating said membrane; and
 percutaneously inflating said containment membrane with said supply of material by way of said hypodermic needle.

12. The method recited in claim 11, comprising the additional steps of attaching said hypodermic needle to one end of a hollow flow tube and locating said flow tube within said hollow piercing instrument behind said uninflated containment membrane, and
 sliding said flow tube from one predetermined position to another through said piercing instrument for successively moving said hypodermic needle into communication with said containment membrane and then moving said containment membrane out of said outer tube means, so that said membrane can be percutaneously infused with and inflated by material by way of said hypodermic needle.

13. The method recited in claim 12, comprising the additional step of interconnecting said source of material to an end of said hollow flow tube opposite said hypodermic needle for percutaneously infusing and inflating said containment membrane with material being supplied from said source by way of said flow tube and hypodermic needle.

14. Apparatus for implanting an inflatable membrane within the subcutaneous tissues of a patient, said apparatus comprising:
 outer tube means having a normally closed cutting end extending thereacross for penetrating the subcutaneous tissues of the patient;
 said inflatable membrane being located within said outer tube means;
 inner tube means slidable through said outer tube means for opening said cutting end after said outer tube means has penetrated the patient's tissues; and
 material dispensing means located at one end of said inner tube means and being slidable with said inner tube means through said outer tube means and into communication with the interior of said inflatable membrane, the sliding of said inner tube means and material dispensing means through said outer tube means opening the normally closed end of said outer tube means and moving said inflatable membrane outwardly therepast, such that said membrane can be percutaneously infused with and inflated by a supply of material by way of said dispensing means and said inner tube means to thereby increase local tissue volume within the patient's subcutaneous tissues.

15. The apparatus recited in claim 14, wherein said material dispensing means is a hypodermic needle.

16. The apparatus recited in claim 15, further comprising:
 a needle stop located at the interior of said inflatable membrane to receive said hypodermic needle and prevent the accidental puncture of said membrane by said needle, said needle stop having at least one opening formed therethrough to permit the delivery of material from said needle to said membrane; and plug means being located at an inlet end of said inflatable membrane for receiving said hypodermic needle therethrough and for forming a fluid-tight closure at said inlet end to prevent the escape of material after said membrane has been inflated and said needle has been removed therefrom.

17. The apparatus recited in claim 14, wherein said inflatable membrane is a genitourinary prosthesis, and the subcutaneous tissues at which said prosthesis is implanted and inflated lies adjacent the patient's urethral mucosa, the inflation of said prosthesis increasing the occlusive pressure applied to the urethra for the treatment of incontinence.

18. The apparatus recited in claim 14, wherein the normally closed cutting end of said outer tube means includes at least first and second cutting members pivotably attached to said outer tube means and rotatable from a closed position across said outer tube means for penetrating the patient's tissues to an open position to permit the movement therepast of said inflatable membrane when said inner tube means and material dispensing means are slid through said outer tube means.

19. The apparatus recited in claim 18, further comprising means for releasably connecting said first and second cutting members together in the closed position to form a non-coring cutting end across said outer tube means.

* * * * *